US011304882B2

(12) United States Patent
Vogel et al.

(10) Patent No.: US 11,304,882 B2
(45) Date of Patent: Apr. 19, 2022

(54) ENERGY RELEASABLE BEAUTY CARE PRODUCTS

(71) Applicants: Audrey Vogel, West Hollywood, CA (US); David Vogel, Scottsdale, AZ (US)

(72) Inventors: Audrey Vogel, West Hollywood, CA (US); David Vogel, Scottsdale, AZ (US)

( * ) Notice: Subject to any disclaimer, the term of this patent is extended or adjusted under 35 U.S.C. 154(b) by 630 days.

(21) Appl. No.: 15/739,959

(22) PCT Filed: Jul. 10, 2016

(86) PCT No.: PCT/US2016/041678
§ 371 (c)(1),
(2) Date: Apr. 16, 2018

(87) PCT Pub. No.: WO2017/008068
PCT Pub. Date: Jan. 12, 2017

(65) Prior Publication Data
US 2018/0344588 A1 Dec. 6, 2018

Related U.S. Application Data

(60) Provisional application No. 62/190,526, filed on Jul. 9, 2015.

(51) Int. Cl.
| A61K 8/04 | (2006.01) |
| A61Q 3/02 | (2006.01) |
| A45D 31/00 | (2006.01) |
| A61K 8/02 | (2006.01) |
| A41G 5/02 | (2006.01) |
| A61Q 5/06 | (2006.01) |
| A61Q 1/10 | (2006.01) |
| A41G 5/00 | (2006.01) |
| A41G 3/00 | (2006.01) |

(52) U.S. Cl.
CPC ............... *A61K 8/044* (2013.01); *A41G 3/00* (2013.01); *A41G 3/0025* (2013.01); *A41G 5/00* (2013.01); *A41G 5/008* (2013.01); *A41G 5/02* (2013.01); *A45D 31/00* (2013.01); *A61K 8/0241* (2013.01); *A61Q 1/10* (2013.01); *A61Q 3/02* (2013.01); *A61Q 5/06* (2013.01); *A61K 2800/412* (2013.01); *A61K 2800/413* (2013.01); *A61K 2800/47* (2013.01); *A61K 2800/805* (2013.01); *A61K 2800/81* (2013.01); *A61K 2800/884* (2013.01)

(58) Field of Classification Search
None
See application file for complete search history.

(56) References Cited

U.S. PATENT DOCUMENTS

| 5,087,494 A | * | 2/1992 | Calhoun | ............... C09J 7/10 428/40.1 |
| 2005/0175648 A1 | * | 8/2005 | De La Poterie | ..... A61K 8/0241 424/401 |

FOREIGN PATENT DOCUMENTS

CN 2380088 Y * 5/2000

OTHER PUBLICATIONS

English translation of CN 2380088 Y (Year: 2000).*

* cited by examiner

*Primary Examiner* — Nicole P Babson

(57) ABSTRACT

The present invention relates to energy-releasable beauty care products. The products are capable of absorbing energy, for example, from an electrical, magnetic, electromagnetic, light, or heat source, which alters the physicochemical state of the beauty care product such that it is easily removable through the utilization of the energy source.

14 Claims, No Drawings

ENERGY RELEASABLE BEAUTY CARE PRODUCTS

RELATED APPLICATIONS

The present application is a National Filing from PCT application PCT/US2016/041678, filed on Jul. 10, 2016, and claims priority from provisional application 62/190,526, filed on Jul. 9, 2015.

FIELD OF THE INVENTION

The present invention generally relates to energy-releasable beauty care products designed to permit attaching and/or removing of the product without physical manipulation of the product such as cutting, filing, or soaking in solvent. More specifically, energy-releasable beauty care product embodiments described herein may be used to easily apply and remove otherwise complicated and difficult to attach and remove products using adhesives. Energy-releasable beauty care product embodiments may be attached or removed by application of select electromagnetic emissions or profiles that change the state of the adhesive. Energy-releasable beauty care products described may include both attachment and removal components which may counteract one another in action if other than the correct transmission is used to effectuate a change in the state of the attachment adhesive.

The beauty care product of the invention may be a nail polish gel, a nail extension, an artificial nail, artificial eye lashes, a wig, or a hair extension.

BACKGROUND

Artificial fingernail and toenail compositions in the form of nail coatings and enhancements are well known and have become a major product line in the appearance and beauty industry. The appearance of one's fingernails (and in many cases also toenails) has become of importance to many fashion conscious individuals or those who wish to correct physical deformities to the natural nail. Commercial artificial nail compositions have been used to enhance the appearance of nails and also to enhance the physical properties of nails, including strengthening fragile nail plates.

Conventional nail coatings may be classified into two categories: nail polishes; also known as lacquers, varnish or enamels and artificial nails; also known as gels or acrylics. Nail polishes typically comprise various solid components which are dissolved and/or suspended in non-reactive solvents. Upon application and drying, the solids deposit on the nail surface as a clear, translucent or colored film. Typically, nail polishes are easily scratched and are easily removable with solvent, usually within one minute and if not removed as described, will chip or peel from the natural nail in one to five days.

Conventional artificial nails are comprised of chemically reactive monomers, and/or oligomers, in combination with reactive or non-reactive polymers to create systems which are typically 100% solids and do not require non-reactive solvents. Upon pre-mixing and subsequent application to the nail plate, or application and exposure to UV radiation, a chemical reaction ensues resulting in the formation of long lasting, highly durable cross-linked thermoset nail coating that is difficult to remove.

Traditional nail polish is mostly comprised of nitrocellulose resins and solvent. Nitrocellulose resins are not known for scratch resistance while the urethanes found in gels have excellent scratch resistance. Nail enamels are generally composed of resins, pigments, dyes, plasticizers, and solvents. Mixtures of low and medium boiling solvents are used to control the rate of evaporation. A high boiling solvent slows the drying process but produces a glossier film; therefore, the drying time of an enamel depends to a large extent on the solvent system. It is obvious to a person skilled in the art that one can speed up the enamel's drying time by substituting polymerizable liquid monomers for the solvent system (i.e., the liquid monomers act as the solvent system for the solid components of the enamel). The enamel is then dried and hardened by polymerization of the liquid monomers using a catalytic system that is triggered by heat or light.

Artificial nails may possess greatly enhanced adhesion, durability, as well as scratch and solvent resistance when compared to nail polishes. However, because of these inherent properties, such thermosets are much harder to remove, should the consumer so desire. Removal typically requires soaking in non-reactive solvents for 30-90 minutes (for acrylics and currently available "soakable gels"; it may take more than 90 minutes (if at all) to remove UV nail gels by solvent and may also require abrading the surface or scraping with a wooden or metal probe to assist the removal process. See U.S. Pat. No. 8,263,677.

Gel manicures are one of the most popular beauty innovations of the last few years—a manicure that lasts for up to two weeks without chipping and doesn't require any dry time. The technology is available from salons and in do-it-yourself versions In general the way gel manicures work is that the color is painted on and then "cured" underneath a UV light. This process is repeated several times per hand—it's what makes the polish ultimately so hard and long-lasting.

The process of applying gels is: first, any existing polish is removed; next a base coat is applied. Between each layer the hand is placed under ultraviolet lights. Often mittens are worn to keep the uv rays off the hands. The polish and top coat are applied as it would be with a traditional nitrocellulose polish. The polish dries completely in the UV light.

Getting the gel off is a difficult problem that has limited the utilization of the gel products. Removal requires 10 or more minutes of soaking in 100% acetone, either in a bowl or individually wrapped with foil. The gel is then scraped off after it softens. The cost of removal and condition of the nails afterwards is a concern. There are also reported cases of bleeding after gels start peeling and then get snagged on something and ripped. The user then has to stick the sore, bloody fingers into pure acetone to get the gel off.

To protect from the harsh, stripping effect of the pure acetone, it is often recommended that one use cuticle oil first to protect skin, then soak the finger tips afterwards in a bowl of vitamin E oil or coconut oil for some quick rehydration.

The word "gel" originally described the nail product's physical state, but over time has become a generic name of the product category. Liquid-and-powder nails are a two-part system in which the powder has already been polymerized to its full-extent, whereas a "gel" is a homogenous product in which the monomers and oligomers (strings of monomers) stay in a semi-liquid/semi-solid state because it hasn't polymerized. "The Science of Gels: What's really going on when your client puts her hand in the nail lamp?" Nails Magazine by Sree Roy, Mar. 14, 2011 accessed at nailsmag.com and incorporated by reference in its entirety (hereinafter "Roy").

Gel nails first appeared in the U.S. in the early 1980s, but were met with limited success until the gel compositions and UV lights were designed to work together with a precise light wavelength and intensity. Currently, gels are one of the most common services to salon menus. Additional innovations in gels have appeared, including 3-D gels, soak-off gels, and polish-gel hybrids. All of these products may be used in the instant invention. Sree.

UV gel nails are basically acrylics which are monomers and/or oligomers and/or polymers used to create nail enhancement products, including UV gel nails (acrylates) and acrylic (liquid-and-powder) nails (methacrylates). Wraps and tip adhesives are also forms of acrylics in the cyanoacrylates category. Roy.

Originally gels were very difficult to remove due to high levels of polymer cross-linking. Newer formulations are less cross-linked and thus more susceptible to acetone but at the same time are less durable. Roy.

Both acrylic nails and gel nails cure with a free radical reaction. In the case of acrylic nails the curing is initiated when the peroxide in the powder is exposed to the reactive monomer in the liquid. With Gel nails the curing is initiated when the photoinitiator in the resin reacts with the wavelengths emmited by the lamp. Photoinitiators are ingredients that absorb light and convert it into the energy needed to drive the polymerization process. Roy.

Hybrid brush-on gel polishes incorporate the same types of solvents as nail polish, which allows them to soak off faster than the current group of soak-off "potted-jar" gels, plus the hybrids have other ingredients to lower the viscosity so that application is more similar to that of a polish. Roy.

Additional ingredients used in gels may be stabilizers, inhibitors, pigments, and resins, and solvents. Stabilizers are chemicals that are added to prevent discoloration. Inhibitors are ingredients that prevent the gel from prematurely hardening or pre-polymerizing while still in its original container. Pigments are insoluble, finely ground substances that impart color. Certain pigments (like white pigments) reflect some of the light that is used to cure the gels, while others (like black pigments) absorb some of UV light, and some just don't cure well at all (many pigments fall under this category). It takes significant research to determine which pigments should be used for UV nail gel. Resins are functional fillers added to modify the properties of the gel, such as thickening or toughening the product. Solvents are substances in which other substances are dissolved. Brush-on gel polishes tend to incorporate an increased amount of solvents to help them break down faster than traditional soak-offs. Roy.

Typical polish ingredients are described in "Polish College: The Basics—An introduction to common nail polish ingredients." by Doug Schoon, Dr. Vivian, B. Valenty, and Paul Brys Jun. 1, 2008 accessed at Nailsmag.com Jul. 5, 2015:

1. Polymers make up the backbone of the polish, and they consist of two main chemicals, Tosylamide/Formaldehyde Resin (TSF Resin) and Nitrocellulose. These two work together to produce the characteristic hard shiny surface and strong adhesion that is typical in all polishes. Nitrocellulose is a primary film former; it creates the hard shiny surface of polish but is brittle when used on its own; the polymer comes from cotton or wood chips by way of a chemical reaction of nitric and sulfuric acids. Tosylamide/Formaldehyde Resin (TSF Resin) is a film former that works with nitrocellulose to reduce brittleness, improve adhesion, and create a more durable polish. (Note that this is not formaldehyde. Formaldehyde is a clear colorless gas that is not used in nail polish. It is found only in small trace amounts as a contaminant in the resin, usually less than 0.05%. You will never find formaldehyde listed as an ingredient in nail polish.)

2. Plasticizers make the polish more flexible and increase the durability of the polish. Dibutyl Phthalate (DBP) and Camphor.

3. Solvents help make the liquid polish spreadable. They keep the ingredients consistently dissolved in the polish during application, but slowly evaporate away after the polish has been applied. Solvents evaporate at different rates, so many solvents are used together to create an ideal evaporation time. Solvents include Ethyl Alcohol, Isopropyl Alcohol, Ethyl Acetate, Propyl Acetate, Butyl Acetate, Toluene, Stearalkonium Bentonite, Benzophenone, and Dimethicone.

4. Pigments are used to create the color of each polish. A combination of naturally occurring and manufactured pigments are blended together to create varying shades. Pigment ingredients include Mica, Silica, Titanium Dioxide, Bismuth Oxychloride, Citric Acid, Ferric Ammonium Ferrocyanide, D & C Red #6 Barium Lake, D & C Red #7 Calcium Lake, FD & C Yellow #5 Aluminum Lake, CI 777266, CI 77891, and CI 15880.

5. Hard gels, or pre-mixed monomers that cure to become polymers either by broadband UV or narrow band LED produced UV light can be used as an overlay with tips, on natural nails, to sculpt and lengthen a nail, or to provide a final layer on acrylic for a shiny, sturdy finish. Gels are also highly resistant to acetone and other harsh chemicals—generally, and "traditionally" the only removal method is filing, rather than soaking. But there are many newer gel-based inventions on the market (soft gels, gel-polish, soak-off gels). "Chemist's Corner: Traditional Gel—With so many newer gel-based inventions on the market (soft gels, gel-polish, soak-off gels), how does hard gel stand out?" Director of research and development at Nubar, Dr. Norair Arkoian, and Light Elegance president Jim McConnell explain it all. by Brittni Rubin, Mar. 18, 2014—accessed at nailsmag.org May 15, 2005. (hereinafter "Arkoian and McConnell").

The difference between gel, soak-off gel, and gel-polish is basically the product's ability to soak off. Technically, traditional gel is a much harder product that needs to be filed off, but that's where all gels start. The soak-off version is made by adding some other ingredients to weaken the hard gel formula, making it able to dissolve in acetone. Gel-polish soaks off similarly but is a less viscous product, which means it's thinner and acts more like nail polish than gel in its application. Soak-off gels are designed and formulated with a higher molecular weight and elongated molecular structure. This creates space between the cross-linked agents, allowing penetration of solvents, which break down the gel. For traditional hard gel, the base has a tighter molecular structure and low molecular weight, making it highly resistant to acetone.] Arkoian and McConnell.

Traditional UV-cured gel is very strong. With traditional gel, you can form nails, build nails, and create decorative art like flowers or objects, whereas gel-polish or soak-off gel are much weaker and might not be able to withstand that. Arkoian and McConnell.

The major difference between using traditional gels or acrylics to build nails is the way the product is applied. Hard gel must be applied in thin layers, or in a thick building layer, and then cured, whereas acrylic is a monomer and polymer system that cures without a UV lamp. But overall, traditional gel and acrylic are quite similar in cured, physical characteristics. Although there are basic technical differences, they tend to have similar end results and can be combined together in one nail or used as two separate systems. Arkoian and McConnell.

Gel-polish, also known as the "chipless manicure," is arguably one of the biggest nail industry inventions in the last decade. The idea of a system that lasts two or three times the duration of regular polish yet is removable without files or heavy soaking has wowed techs and clients alike. "Chemist's Corner: Gel-Polish—Getting behind the science of gel-polish is no easy feat, but with a better framework for its chemistry comes improved technique and the ability to educate clients. NAILS picked the brain of OPI's Dr. Paul Bryson for some user-friendly answers" by Brittni Rubin, Feb. 21, 2014, accessed at nailsmag.org May 5, 2015. (Hereinafter "Bryson").

Soak-off gel-polish is mainly made of urethane methacrylates (or acrylates). Gel-polish cures by "polymerization," meaning the formula's molecules react by linking up with one another into large chains called polymers. Crosslinks, or chemical bonds that connect different polymer chains together, are also created, resulting in a structurally strong molecular network. By contrast, lacquer doesn't cure, it dries—the polymers in lacquer are simply left behind on the nail as the solvents evaporate. A hybrid product, such as CND's Shellac or OPI's UV-Cure Topcoat, undergoes curing and drying. Bryson.

When light hits the gel-polish, a UV-sensitive molecule called a photoinitiator chemically starts the curing reaction. Think of the photoinitiator as a "lighting rod" that captures a bolt of UV energy. More technically, the photoinitiator has a chemical bond that's easily broken by UV, and when it's breaks, the fragment of the molecule (or a "free radical" in chemistry lingo) is very reactive and bonds to the nearest methacrylate, which causes it to bond to another and another, resulting in a cure. Bryson.

The "free radical" curing process is subject to oxygen inhibition, which means the oxygen in the air prevents the molecules at the surface from polymerizing. So right at the very surface, there's an uncured layer. It happens with all acrylics, even liquid-and-powder systems, but it's more noticeable with gel-polish and low-odor liquid-and-powders since the larger molecules are more easily inhibited. Bryson.

Gel-polish requires UV light to start the chemical curing reaction. Without UV light, it won't cure and will stay wet for a very long time until the methacrylates deteriorate, which could take months or even years. Bryson.

Traditional gels were mainly made for sculpting. They need good structural strength, so they're highly crosslinked. Soak-off gels have to be made with fewer crosslinks because too many creates a tight polymer network that can't be penetrated easily by acetone, which would make the product much slower to soak-off. Bryson.

U.S. Pat. No. 4,260,701 discloses Improved composition for a fingernail coating having an acrylic binder, a peroxide catalyst, a tertiary amine accelerator, and a polymeric filler at least partially soluble in the coating. The acrylic binder contains a monoethylenically unsaturated monomer comprising at least a major proportion of methoxyethyl methacrylate. A polyfunctional monomer may be present that copolymerizes with the monoethylenically unsaturated monomer, for crosslinking and toughening.

U.S. Pat. No. 4,704,303 discloses a combination of a human nail and an artificial nail cover coated by first applying to the surface of the combination a monomeric aliphatic or cycloaliphatic hydrocarbon urethane dimethacrylate, a photo cure system and methacrylic acid and then curing in the visible light range and then applying a composition of the monomeric urethane or methacrylate, a polymeric aliphatic of cycloaliphatic hydrocarbon urethane acrylate methacrylate, a low viscosity polyglycol dimethacrylate and a photo cure system and curing in the visible range.

U.S. Pat. No. 5,637,292 discloses water based UV curable human nail coatings. The formula is: aliphatic waterborne urethane containing 40% solids in water with N.N-Diethylethanamine, acrylated urethane containing 50% polymer of alkyl carbomonocycle diisocyanate with alkanepolyol polyacrylates and 50% acrylated polyol, isopropanol, propylene glycol methyl ether acetate, 2-hydroxy-2-methyl-1-phenyl-1-propanone, hydrolyzed keratin at 125,000 molecular weight 13% solids in water with 2% propylene glycol, protein hydrolyzate from milk. These ingredients are placed in a plastic mixing container in the given order then thoroughly mixed for 10 minutes or until all visible lumps and droplets are no longer visible.

U.S. Pat. Nos. 6,391,938 and 6,599,958 disclose light cured nail coatings that are applied to natural nails and/or artificial nail-tips for cosmetic purposes. An optional bond-enhancing compound can be used to strengthen the bond between the light curable coatings and the natural nail. Also, finishing compounds may be used to clean the surface of the uv curable coatings resulting in a high-gloss shine. The methods of applying uv-radiation curable nail coatings, bond-enhancing compounds, and finishing compounds to artificial nail-tips and natural nail are also discussed.

These patents disclose radiation curable natural nails and/or artificial nail tip coating compositions comprising: a polymeric compound; a photoinitiator; a photoaccelerator; and at least one adhesion promoting polymer, said polymer comprising methacryoyloxy ethyl phthalate. The composition may also include a coupling agent, and plasticizers, secondary photoinitiators, colorants, dyes, inhibitors, filers, fibers and adhesion promoting polymers. The polymeric compound is an acrylate or methacrylate.

U.S. Pat. No. 6,803,394 discloses a composition for actinic radiation curable nail coatings and artificial nail tips comprising a BISGMA based urethane resin, an additional polymer, and a photoinitiator.

U.S. Pat. No. 4,574,138 discloses a rapid cure polymerizable monomer sealing and bonding compositions are disclosed. The polymerizable compositions comprise at least one polymerizable acrylate monomer system comprising a urethane acrylate monomer having vinyl reactive ends, and at least one hydroxy-terminated, monofunctional, short chain monomer which is soluble in or miscible with the urethane acrylate monomer; an effective amount for initiation of a free radical initiator; and a compatible filler material.

U.S. Pat. No. 4,421,881 discloses lacquer compositions which provide desirable characteristics in the durability and hardness of the resulting coatings. More particularly, this invention discloses nitrocellulose-resin based lacquers which contain small amounts of both a high molecular weight mixture of water-soluble gelatins derived from animal bone and hide and an acrylic copolymer and conventional additives. The lacquers are used for human nail coatings.

U.S. Pat. No. 4,205,018 discloses a resin composition is disclosed comprising, as essential ingredients, (I) a urethanized epoxy resin or a urethanized epoxy resin acrylate or methacrylate, (II) a ketone resin and (III) a cross-linkable polymerizable compound containing at least two ethylenically unsaturated groups. This disclosure relates to a resin composition curable by actinic radiation which does not substantially contain an acid group and has good adhesion, flexibility.

U.S. Pat. No. 8,263,677 and related patents disclose a nail coating system comprising a reactive basecoat adhesion layer, an intermediate, decorative and reactive color layer, and a protective and reactive topcoat.

Light curable nail coatings are disclosed in U.S. Pat. No. 5,194,292, entitled "Method of Drying and Bonding Nail Polish." The patent describes a method of protecting common nail polish by applying a light-curable clear coating over the polished nail.

Light curable nail coatings are disclosed in U.S. Pat. No. 4,704,303, entitled "Nail Extension Composition". The patent describes a coating composition based on an aliphatic or cycloaliphatic hydrocarbon urethane diacrylate or (meth)acrylate having a molecular weight of 250 to 500 and a viscosity of 5,000 to 30,000 cps. Radiation in the visible region is used to cure the coatings disclosed in the patent.

Light curable nail coatings are disclosed in U.S. Pat. No. 4,682,612, entitled "Novel Process and Article for Preparing Artificial Nails." The patent describes an organic solvent-free photocurable composition that has at least one liquid monomer in which an acrylated urethane oligomer is dissolved and crosslinked upon curing. Radiation in the ultraviolet (UV) region is used to cure the coatings disclosed in the patent.

Publication WO 2001043579 discloses the use of Bisphenol A Diglycidyl (Meth)Acrylate ("BISGMA") based urethane resin.

Nail gels are generally made from polyurethane metalacrylate prepolymers of resins, polyurethane acrylate prepolymers of resins, Di-HEMA trimethylhexil of bicarbonates, trimethyleneglycol of dimetacrylates, where the components like benzophenon are contained. Coloured pigment is added to the basic gel for achieving the various colours and shades of these materials and often a glucocorticosteroid is added to the gel for treatment of bacterial infection or mold of nails. Publication WO 2013004204.

U.S. Pat. No. 5,435,994 discloses a photo-reactive nail polish coating composition that cures quickly upon exposure to low levels of ultraviolet radiation. The coating consists of a polymer formed from a composition comprising nitrocellulose, a photo-reactive monomer, a photoinitiator and a reaction inhibitor, resulting in a product compatible with commercially available nail polish of any color and removable by standard acetone-based polish removers. It is also compatible with every-day chores because it is insoluble in water. The composition is not phototoxic and has very low potential for skin irritation or sensitization. The photo-reactive coating is applied over the wet nail polish and then irradiated with safe dosages of ultraviolet radiation, causing the nail polish to dry in a few minutes.

U.S. Pat. Nos. 3,896,014 and 3,928,113 to Rosenberg (1975) disclose a process for coating nails comprising the steps of applying a water soluble base coat to the nails, allowing the base coat to dry, then applying a photocurable nail lacquer and curing the lacquer by exposing it to sufficient amounts of radiation. The inventive purpose behind this patent was to try to develop a nail coating that could be removed by water instead of an acetone based commercially available nail polish remover. Accordingly, the nail lacquer was specifically designed for a water soluble base coat, and commercially available nail polishes could not be used in the process. The water soluble base coat that rendered the photocured composition strippable also made the cured film incompatible with daily human functions such as hand and dish washing, bathing, and all other activities involving the immersion of nails in water.

U.S. Pat. No. 4,596,260 discloses a process of applying a photocurable coating to an artificial nail tip whereby upon exposure to suitable radiation the coating hardens to give the appearance of a natural nail. As it consists of a polyfunctional polymer to which the monomer is crosslinkable, the photocurable coating is very difficult to remove if applied on top of commonly used nail polishes.

U.S. Pat. No. 4,126,675 teaches a nail polish composition including a copolymer resin based on a mixture of methyl methacrylate and hexyl methacrylate. These two substances are mixed separately and caused to polymerize to form a copolymer under specific conditions before they are added to the balance of the ingredients comprising the nail polish. No polymerization occurs after the copolymer resin is mixed with the balance of the ingredients or after the resulting nail polish is applied on the nails of a user.

US Patent Publication US 20090126753 discloses adhesives for wig, wig using the same, and methods of manufacturing.

U.S. Pat. No. 8,881,741 discloses devices, methods, and systems for dispensing artificial eyelash adhesive for attaching an artificial eyelash to a natural lash line, and to methods of applying artificial eyelashes. Disclosed is an artificial eyelash adhesive dispenser comprising a backing layer, an artificial eyelash adhesive tape layer having a bottom surface adjacent to the backing layer and a peelable protective top layer over the top surface of the eyelash adhesive tape layer. The dispenser further includes a plurality of cuts extending through at least the adhesive tape layer and the peelable protective top layer so as to form a tear line along which an individual strip may be separated from a remainder of the dispenser. The adhesive tape layer is chemically formulated so as to not irritate the skin or eyes. Wig tape is one such material that is particularly suitable.

Artificial eyelashes are disclosed in U.S. Pat. No. 2,835,259.

Artificial eyelash and adhesive coloring device for eyelids is disclosed by U.S. Pat. No. 3,266,500.

U.S. Pat. No. 6,029,674 discloses an adhesive device for attaching a false eyelash to an eyelid.

U.S. Pat. No. 6,308,716 discloses an adhesive device for attaching a false eyelashes.

U.S. Pat. No. 6,733,856 discloses double eyelid forming tape or string and a method of manufacturing the same.

US Patent Publication No. 20050061341 discloses false eyelashes.

US Patent Publication No. 20060144413 discloses double-faced adhesive tape and wing with the same.

US Patent Publication No. 20090126753 discloses an adhesive for a wig and methods of manufacturing.

US Patent Publication No. 20100043816 discloses medical double-sided false eyelash tape.

DE-A4328108 describes an adhesive for floor coverings and a process for taking up the bonded floor coverings using microwave energy. To this end, the adhesive is said to be electrically conductive and softenable by a microwave unit. Solventless contact adhesives based on (aqueous) polymer dispersions containing copper powder or aluminium powder are specifically mentioned. According to the teaching of this document, the adhesive bond securing the pieces of floor covering can be dissolved by application of a microwave unit to soften the adhesive layer so that, after the layer of adhesive has softened, the pieces of floor covering can be manually removed.

WO 94/12582 describes a contact adhesive based on a mixture of an aqueous polymer dispersion, an adhesive dissolved in an organic solvent, tackifiers and finishing agents. This contact adhesive has constant adhesive strength over a broad temperature range and enables the adhesive bonds to be mechanically separated. According to the document in question, the adhesive is suitable for bonding insulation and/or parts of decorative surfaces, for example insulating materials or plastic films.

DE-A-19526351 describes a dissolving gel for lacquers, paints and adhesives based on organic solvents containing additions of wetting agents, thickeners and other typical auxiliaries. The use of the gel as a remover in the stripping of two-component lacquers is mentioned as a specific application. Although it is stated that the mixtures in question may also be used for two-component adhesives, there is no specific reference to the dissolution of the adhesive bonds. Similarly, WO 87/01724 describes a composition for removing hardened polysulfide sealants or coatings. In this case, an alkali metal or ammonium thiolate based on alkyl or phenyl thiolates is dissolved in a solvent or solvent mixture consisting of dimethyl formamide or dimethyl acetamide or a mixture thereof with aromatic solvents, such as toluene or xylene, and the resulting solution is applied to hardened polysulfide sealants or coating materials so that they may subsequently be removed from their substrates, such as aircraft tanks for example. Particulars of the dissolving of adhesive bonds are not disclosed.

DE-A-35 01 490 describes a sheet of glass bonded into the frame of a car body using an elastomeric crosslinked adhesive. On its surface, the sheet of glass is provided in the bonding zone with a conductive strip which is equipped with electrical terminals and which, on its side facing the adhesive, carries a parting layer of a heat-meltable material, such as soft solder or thermoplastic. To reverse the adhesive joint, current is applied to the conductive strip which heats up, the parting layer melts and the sheet of glass can be removed from the body.

EP-A0521825 describes a dissolvable adhesive bond where the parts joined to one another are bonded by a strip of adhesive applied between them. This strip of adhesive contains a flat thermoplastic separating element which in turn contains intrinsically conductive polymers, electrically conductive carbon blacks, graphite, metal powder, metal fibers or metal needles, metal-coated fillers, metal-coated glass microbeads, metal-coated textile fibers or mixtures of these materials. When the adhesive bond is heated by electrical current or heat, this thermoplastic separating layer is softened so that the parts joined to one another can be mechanically separated. According to the document in question, these dissolvable adhesive bonds are suitable for direct glazing in car manufacture.

U.S. Pat. No. 6,855,760, incorporated herein in its entirety by reference, discloses adhesive compositions where the binders contain nanoscale particles with ferromagnetic, ferrimagnetic, superparamagnetic or piezoelectric properties. The adhesives may be dissolvable adhesive bonds Where the bonded parts are joined together by a layer of adhesive introduced between them, the adhesive matrix of the adhesive layer containing nanoscale particles. The disclosure also relates to a process for dissolving adhesive bonds using electrical, magnetic or electromagnetic alternating fields, the adhesive layer containing nanoscale particles which heat the adhesive layer under the influence of these alternating fields. The effect of this heating of the adhesive layer is to separate the adhesive bonds.

Thus, while these references (all of which are incorporated herein in their entirety by references) are relevant to show the general state of the art, they are not directed to the inventive purpose behind the subject invention.

Against the background of technology, the problem addressed by the present invention was to provide cosmetic adhesives and systems which would enable strong adhesive bonds to be efficiently dissolved. After the corresponding substrates have been bonded with these adhesives, the bond would lend itself to heating by application of energy to dissolve or soften the adhesive bond.

There remains a need for a cosmetic product that possesses the enhanced adhesion properties and durability of gels, yet also possesses the ease of removal more similar to that of nail polishes.

DETAIL OF THE INVENTION

The energy-releasable beauty care products of the present invention relates to beauty care products that may be applied in conventional means or by unique mechanisms described herein, but are removed or released using energy or electromagnetism. The release of the beauty care product may be by means of an externally applied stimulus, and in an advantageous embodiment by way of an electromagnetic transmission to the beauty care product of a defined wavelength, strength, and/or pulse spectrum. Suitable stimuli may also comprise a magnetic or electrical stimulus. Energy-releasable beauty care products of the present disclosure include assemblies having more than one attachment component.

In certain preferred embodiments, the beauty care products of the invention are nail gels (including but not limited to gel polishes, extensions, and false nails), hair extensions, wigs and other hair replacements, false eye lashes, and eye lash extensions.

The attachment systems of the invention may comprise one or more adhesive materials. To effectuate distribution of the energy of the transmission throughout the adhesive, the adhesive may further comprise one or more energy distribution components, which may be associated with one or more surfaces of any adhesive layer, and/or distributed uniformly or non-uniformly in the beauty product itself. Such energy distribution component may comprise, for example, a metal layer or metal quantum dots which are receptive to the transmission. The energy distribution components may convert the transmission energy into a second form of energy, such as converting a radio wave transmission into heat, thus acting as an energy converter. The second form of energy may cause a change in a physical property of the adhesive material composition that permits the attaching or removing. Thus, the resulting change in one or more physical properties of the adhesive (such as tackiness, bonding strength, density, etc.) may be used to remove the product or product assembly.

In some embodiments, the energy-releasable beauty care products may comprise additional attachment components which may, for a non-limiting example, provide reattachment capabilities. For example, a first attachment component may comprise an adhesive system that changes in density when exposed to a particular energy transmission (for example, increasing in volume for the same mass of adhesive material when exposed to a wavelength of x) wherein the density change induces removal of the product. A second attachment component may comprise an adhesive system that is activated to an adhesive state, or wherein a density change occurs when exposed to a particular energy transmission, such as exposure to a wavelength of y, wherein such attachment component adheres when exposed to the wavelength of y.

The energy-releasable beauty care products may also include features to defeat attempts to copy the product. Examples of copying attempts may include exposure to environment or external fields not complying with the characteristics of the prescribed field profile. Thus in certain embodiments, the energy-releasable beauty care products provide removal by requiring the application of a magnetic, electrical or electro-magnetic field having a prescribed profile (that is, for example, based upon the composition of the attachment adhesive system) to effect the application/removal functions. The configuration of the energy-releasable beauty care product, and its constituent attachment elements, determines the field profile required for operation. The configuration of each product, or group of products, may be designed to respond to a unique profile, the characteristics of which are kept secret, thereby implementing a unique "key" for the product and foiling copy cat products. The prescribed profile may include, without limitation, specification of field type, frequency, field strength, power level, and time waveform characteristics. For some embodiments, sequences of fields, each having a different profile, are anticipated as attributes of the key.

Alternatively, or in addition, the simultaneous application of multiple fields, each having a different profile, may be required as a key. An additional element of the key may be a requirement for specific physical orientations of the application of the field key. Thus the system can be sold as a difficult to copy system comprising both nail gels or extensions, wig, or lashes together with a UV light and electromagnetic apparatus.

In one embodiment, exposure to the prescribed field causes the adhesive attachment element bond to completely release allowing separation without the application of additional mechanical or chemical force. In other embodiments, the adhesive attachment element may be configured to only weaken, in response to exposure to the field, wherein additional external mechanical force must be applied to remove the product. Thus the amount of heat energy generated can be controlled to ensure customer comfort and safety. For example, the energy-releasable beauty care product may comprise a transmission sensitive adhesive with or without one or more energy distribution components (which may be energy converter components) that binds the product to the customer. By exposing the product to a transmission that activates the adhesive to a less adhesive state, the product can now be much more easily removed by a consumer (avoiding the need to pull out the scissors and/or files.

In yet another energy-releasable beauty care product of the present disclosure, use is made of an electrically-releasable adhesive between two substrates capable of holding a charge. In one such embodiment, the electrically-releasable adhesive comprises polymers capable of adhering such substrates to a surface of the adhesive wherein at least one polymer is polar and at least one polymer is non-polar. Such electrically-releasable adhesive further may comprise one or more electrically conductive material, for example, selected from the group consisting of one or more of a conductive salt, metal particles, metal wires, nanowires, and carbon nanotubes. By appropriate selection of the polar and nonpolar polymers and the electrically conductive material, one may provide an electrically-releasable adhesive composition that is capable of transitioning from a first state to a second state in response to the application of external electrical and/or magnetic energy ("electro-magnetic energy"). The external energy may be a specific profile of electro-magnetic energy such as an applied voltage. In an embodiment, the first state is a first adhesion state and second state is a second adhesion state, for example, wherein the first adhesion state has a different density than the second adhesion state.

An electrically-releasable adhesive may also be used in an embodiment energy-releasable beauty care product employing composite magnetostrictive and electrostrictive layers ("ME composite"). In such embodiment the adhesive comprises polymers capable of adhering such substrates to a surface of the adhesive wherein at least one polymer is polar and at least one polymer is non-polar. The electrically-releasable adhesive as above may comprise one or more electrically conductive material, for example, selected from the group consisting of one or more of a conductive salt, metal particles, metal wires, nanowires, and carbon nanotubes. The external energy used to attachment and/or remove may be a specific profile of electro-magnetic energy. In an embodiment, the first state is a first adhesion state and second state is a second adhesion state, for example, wherein the first adhesion state has a different density than the second adhesion state.

In addition, in some embodiments, there may be no residual material left on the customer after the energy-releasable beauty care product system has been released. In one non-limiting example, freedom from residue can be effected when an electrically releasable adhesive is subjected to a direct current or DC biased field, the product is conductive or features a conductive film thereon, the protection structure is conductive or features a conductive film thereon, and the product or its film and the protection structure or its film respectively serve as the anode (connected to the positive charge) and cathode (connected to the negative charge). In this example, after debonding the anodic surface may be free of adhesive residue.

In certain embodiments, there is provided an energy-releasable beauty care product comprising one or more energy-releasable beauty care product components. The energy-releasable beauty care product assembly can be employed to allow the easy application and removal of beauty care products such as nail gels and extensions, eye lashes, and replacement hair such as extensions, wigs, etc. The energy-releasable beauty care product assembly may be implemented as a separate module coupled to the product itself or a structure coupled to the product. It may also form part of the product, being integral therewith.

Attachment components in embodiments may comprise one or more transmission activatable-adhesive and/or removable elements. Attachment components may further comprise mechanical mechanisms and structures that interfere with the use or full use of the product.

Attachment assemblies may be designed such that upon activation with the appropriate energy, or profile of energies, 1) one or more adhesives associated with the assembly move from an attachment state to a removal state and 2) one or more adhesives associated with the assembly move from a removal to an adhesive or attached state.

In embodiments, actuation of each of the attach/remove functions requires the application of a transmission, such as a field, or fields, having a prescribed profile, the prescribed profile serving as a unique key. The unique key may comprise, for example, one or a combination of magnetic, electric, electro-magnetic, optical, acoustic fields having a prescribed profile. The prescribed profile may include, without limitation, specification of field type, frequency, field strength, power level, and time waveform characteristics.

For some embodiments sequences of fields, each having a different profile comprise components of the key. Furthermore, the simultaneous application of multiple fields, each having a different profile, may be required as a key. An additional element of the key may be a requirement for point or orientation of the application of the field key.

As would be understood by the disclosure herein, the configuration of the energy-releasable beauty care product, and its constituent attachment elements, may determine the field profile required for operation. The configuration of each product, or group of products, may be designed to respond only to a unique profile, the characteristics of which may be kept secret, thereby implementing a unique key for the product.

For energy-releasable beauty care product assembly embodiments providing an ordered sequence of attach/remove operations, each operation of the sequence may require application of a unique field profile. The corresponding sequence of unique field profiles should be configured so that unique profiles, required earlier in the sequence, do not prematurely activate later sequence steps.

In one embodiment of an adhesive attachment beauty-care product a transmission activatible-adhesive is preferred, that is an adhesive that changes in chemical or physical properties ("chemicophysico properties") when exposed to a specified energy, which may be applied by a transmission. The change in chemicophysico properties should be of an extent that the change can be used to effect a change from an attached to removed state, or from a removed to attached state.

The adhesive material composition may be formulated to significantly change at least one of its physical properties (i.e., state change) in response to a particular energy, such as an energy transmission, such as an electrical signal, magnetic field, electromagnetic wave, light, or heat. Effected physical properties may comprise, without limitation, dimensions, volume/density, adhesion, and, tensile, compressive and shear strengths.

In certain embodiments, an adhesive attachment element comprises an adhesive material composition integrated with an energy distributor and/or converter to form a composite structure. The integrated energy distributor helps to distribute the energy throughout the adhesive and may further act as converter transforming a specific externally applied energy (such as an electromagnetic wave) into a second type of energy (such as thermal energy) with the second type of energy being responsible, at least in part, for the change in state of the adhesive.

Energy-releasable beauty care products may be configured to provide any desired combination of attaching/removing/re-attaching/anti-copying features by the employment of either single or multiple attachment elements. The attachment elements may be configured in parallel, where each grouping of elements forms its own interface between the surfaces, or in series, where the grouping of attachment elements is configured as a sandwich between the surfaces. In some embodiments, a remote-activation may comprise both series and parallel grouping of attachment elements. In this way, wigs or hair extensions may be applied, removed, and re-applied for example.

In one embodiment of an easy application beauty product, an adhesive attachment element comprises a laminate of an adhesive material bonded to a first carrier substrate that acts an energy converter. The first carrier substrate may be, for example, a conductive metal-containing layer (such as a layer containing aluminum, iron, steel, copper, gold, platinum) that conducts the energy to a surface of the adhesive material. The adhesive attachment element may bond a surface of product along one surface of adhesive material and also to the customer's nail. Exposure of first carrier substrate to an externally applied field in such embodiment causes the flow of electrical eddy currents. The eddy currents are dissipated, as heat, by the resistance of the metal containing layer. The dissipated heat raises the temperature of the adhesive material which causes the adhesive to de-bond from product.

In an additional embodiment of release adhesive there is disclosed an electrically releasable adhesive comprising at least two polymers, at least one polymer that is polar and at least one polymer that is non-polar, and an electrically conductive material comprising one or more of the following materials: conductive salt, metal particles, metal wires, nanowires, and carbon nanotubes, and characterized by a transition from a first state to a second state in response to the application of external energy. The external energy may be a specific profile of electro-magnetic energy such as an applied voltage. In an embodiment, the first state is a first adhesion state and second state is a second adhesion state. The different states may, for example, be a change in the physical volume of the adhesive or in the adhesion strength.

Adhesive additives which can be particles or films are selected, without limit, from aluminum, copper, iron, epoxy and wax to control thermal diffusivity which allows formation of part of a key by managing thermal energy transfer and by effectively establishing thresholds for the input energy. Thus a very specific rate of energy and time is required to reach a particular thermal threshold given by a collective set of properties. The magnitude of the difference in properties means that small additions of material from 0.5% to 10% can make a substantial difference in performance.

In a further embodiment, there is disclosed a remotely controllable release adhesive system comprising: an ME (magnetostrictive/electrostrictive) layer and an adhesive layer comprising at least two polymers, at least one polymer that is polar and at least one polymer that is non-polar, and an electrically conductive material comprising one or more of the following materials: conductive salt, metal particles, metal wires, nanowires, and carbon nanotubes, and characterized by a transition from a first state to a second state in response to the application of external energy. Magnetostrictive is a property of ferromagnetic materials that causes them to change their shape or dimensions when subjected to a magnetic field. Electrostrictive is a property of all electrical non-conductors, or dielectrics, that causes them to change their shape under application of an electric field. The external energy may be a specific profile of electro-magnetic energy. In an embodiment, the first state is a first adhesion state and second state is a second adhesion state.

A remote-activation adhesive attachment in another embodiment comprises two carrier substrates which sandwich adhesive material to form a sandwich or multi-layer energy-releasable beauty care product with carrier substrate being bound to protection structure, and protection substrate being bound to the customer's nail, hair, scalp, or eye lashes as desired in the specific application. When carrier substrates are conductive substrates the two conductive substrates may act as an energy converter. This energy converter functions to provide either purely enhanced heating or in another implementation, an electrostatic field. The unique key for the attachment may be implemented by a prescribed field profile, which may be defined by physical and electrical properties of the energy converter in combination with the thermal properties and temperature related state change characteristics of the adhesive material.

An example of an adhesive material composition suitable for application in this embodiment adhesive attachment element comprises an admixture of an adhesive and particles of non-adhesive material dispersed through the adhesive.

The actual adhesive is chosen based on a combination of the manufacturing and product attachment requirements. For example, one "base" adhesive appropriate for use with a attachment application is the Raymat 8303A UV cure acrylic pressure sensitive adhesive (manufactured by Raymat Materials, Inc. 30081 Ahern Ave, Union City Calif. This adhesive is convenient because it is nominally a fluid and thus additional components can be conveniently added. It is applied as a liquid to a metal-containing layer and ultraviolet energy is used to effect a cure to a tacky state. A release liner which can be peeled off with just light force may be attached. This release liner can be similar to a waxed paper or silicone film to which the adhesive will not strongly adhere. This permits easy assembly as a pseudo tape. This tape can now be conveniently used in an attachment assembly in which it is securing a latch for example to which it strongly adheres. However, one could also use a base adhesive such as an epoxy-amine when convenience of attachment and assembly is not the issue but strength is of primary importance. One skilled in the art can easily imagine embodiments for inclusion in nail gels all the way to "stick-on" hair extensions, wigs and false eye lashes.

The particles dispersed through the adhesive may modify the properties of the adhesive material, help distribute the heat energy more effectively, and/or, provide an additional first energy source to second energy source conversion mechanism (such as from electromagnetic energy to heat energy conversion). In addition, other dispersed particles may exhibit a desired physical behavior, in response to the externally applied field. In an embodiment, the dispersed particles may serve to modify the thermal conductivity properties of the admixture either enhancing or retarding heat flow within the adhesive. Metal particles characterized by high thermal conductivity may enhance heat flow while non-metallic particles may retard heat flow.

In another embodiment, electrically conductive particles, having dimensions resonant at the externally applied field frequencies may function as energy converter elements. The electrically conductive particles, when excited by a resonant field, may, for example, generate heat via resistive dissipation of induced eddy current or frictional effects due to acoustic resonance of magnetic particles. In a further embodiment, the dispersed particles may physically expand in response to exposure to the externally applied field. Physical expansion of the dispersed particles would result in the mechanical fracturing of the adhesive attachment element bond thereby releasing the nail gel, wig or eye lashes.

In certain embodiments, adhesive material compositions may comprise hot melt adhesives that cure and harden at a specific temperature. A non-limiting example is disclosed in U.S. Pat. No. 6,387,449 which discloses hot melt adhesives comprising an isocyanate compound; a polyester-polyol; a reactive tackifying resin comprising a non-polar polyol having a hydroXyl number of about 50 or less; and a thermoplastic polymer. The adhesives may also include a polyether-polyol that has an average molecular Weight in the range from 1,000 to 10,000 selected from the polyethylene glycols, polypropylene glycols, tetramethylene glycols, polybutylene glycols, and mixtures thereof.

The polar polymer may comprise, for example (without limitation), one or more of the following: polyether polyols, polyester polyols, polycarbonate polyols, or any other polar polyol, or amine-terminated polyols. The non-polar polymer may comprise, for example (without limitation), silicone polyols, fluorinated polyols polybutadiene polyols, carboxy terminated polybutadienes, isocyanate-terminated polybutadienes, and melainized polybutadienes.

An additional energy converter may comprise a foil or a film that is deposited by any variety of methods such as and is a conductive or magnetic material. State-change adhesive compositions and energy converters are configured so that they do not change state in an appreciable manner when exposed to the energy profile intended to remove the product. For example, such compositions may not heat to the temperature required to cure and harden when subjected to the field prescribed for removing the energy-releasable beauty care product.

In an embodiment, an adhesive material suitable for use in the energy-releasable beauty care product may comprise a base liquid adhesive into which may be incorporated thermally expanding particles, and/or RF-susceptible particles, and/or thermally conducting particles.

In the energy-releasable beauty care product, release may need to be rapid (for example, 2 seconds or less) and complete (clean) across the surface of adhesive. When using RF induction to generate a rapid release, and specifically with adhesives which often have poor thermal conductivity characteristics, temperature gradients develop. In addition, some energy-releasable beauty care product systems require operation in a narrow range of conditions. To address the problem of thermal gradients, thermally conducting particles may be dispersed within the adhesive help conduct the energy, for example thermal energy, generated by the energy converter film and/or RF susceptor particles. When the temperature of the adhesive reaches a certain point, the energy responding particles may be selected such that they dramatically increase in size, breaking the chemical bond between adhesive layer and an attached substrate.

Subject to the general rules and limitations regarding cosmetics and beauty products, the base liquid adhesive that makes up adhesive may be of any general class of polymers or polymer resins used in bonding such as epoxy, acrylic/methacrylic resins, two-part or one-part polyurethane, one- or two-part silicones, polyester, polyamide, polyurea, phenolic resins, melamine formaldehyde condensates, and/or alkyd resins or mixture thereof. The adhesive cures over time at a temperature that is lower than that which could release. It may be desirable to have adhesives with low thermal inertia and low specific heat up to the release point of the thermally expanding particles in order to have rapid heating.

The thermally expanding particles or liquid droplets may be inorganic particles such as ammonium carbonate, ammonium hydrogen carbonate, sodium hydrogen carbonate, ammonium nitrite, sodium borohydride, and azide compounds. The thermally expanding particles or liquid droplets may also comprise water, alkane chlorofluorides, e.g., trichloromonofluoromethane and dichloromonofluoromethane; azo compounds, e.g., azobisisobutyronitrile, azodicarbonamide, and barium azodicarboxylate; hydrazine compounds, e.g., p-toluenesulfonyl hydrazide, diphenylsulfone-3,3'-disulfonyl hydrazide, 4,4'-oxybis(benzene sulfonyl hydrazide), and allyl bis(sulfonyl hydrazide); semicarbazide compounds, e.g., p-toluoylenesulfonyl semicarbazide and 4,4'-oxybis(benzene sulfonyl semicarbazide); triazole compounds, e.g., 5-morpholyl-1,2,3,4-thiatriazole; and N-nitroso compounds, e.g., N,N'-dinitrosopentamethylenetetramine and N,N'-dimethyl-N,N'-dinitrosoterephthalamide.

The thermally expanding particles or liquid droplets may also comprise microspheres, heat-expandable fine particles prepared by the encapsulation of a gaseous component in a polymer shell. The gaseous component expands within its shell upon the application of thermal energy. Gas agents such as butane, propane, heptane and the like are preferred as the gaseous component due to ease of mixing operations. Commercially available heat-expandable microspheres, such as those sold under the name Expancel Microspheres® (Nouryon, Inc), comprised of a thermoplastic acrylic resin polymer and core of a spherical plastic particle composed of alkane gases, may also be used. Additionally, polystyrene-encapsulated water may also be used as a thermally expanding particle. As sold, the particles generally have a particle diameter of 1 to 100 micrometers, but it may be in embodiments that a narrower distribution of particle diameters should be employed. For example, a complete and effective release of the adhesive upon heat treatment may occur with fine particles having a certain average particle diameter of 5-40 um.

Tuning of the release temperature may be accomplished by changing the polymer shell surrounding a microsphere. Depending on the shell's composition, the microspheres may expand between room temperature up to 200 degrees Celsius, but between 50-80 degrees Celsius may be preferred in order to provide for a safe and comfortable customer experience.

The microsphere shell may be made of polymers such as thermoplastics including acrylonitrile butadiene styrene (ABS). Thermally expanding particles may increase by as much as 40 times in volume.

The thermally conducting particles may include metal such as copper or an inorganic such as glass. The copper particles are about 100 microns in diameter. An example of an RF susceptor particle is 10% $Zn_2Y$, which is available as FP130™ from the PowderTech Corp. The RF particles may also be magnetic, in which case, heating of the particles may occur mainly by magnetic hysteresis losses rather than eddy currents.

The energy converter may be a material that generates eddy currents in the presence of an alternating magnetic field. Conductor films or foils made of aluminum, 1010 steel, permanent magnet, of copper materials are suitable. In addition, magnetostrictive film subjected to alternating AC magnetic fields will have a varying stress field and also generate heat.

Other embodiments of the inductively releasable adhesive system include the addition of wax particles to adhesive. The wax particles may be incorporated into adhesive in various combinations with thermally expanding sphere, thermally conducting particles, and RF susceptor particles and should be a low % by volume. The wax particles can assist with release of adhesive from an attached substrate such as a nail, hair, the scalp, or eye lashes. Representative waxes include a paraffin wax with a melting point of 47-65 C, which is most desirable, but carnauba wax (melting point of 78-85 C) or bee's wax (melting point of approximately 45 C) may also be employed. Other suitable waxes are known and will be known to one skilled in the art.

The present invention also relates to dissolvable adhesive cosmetics where the bonded parts are joined together by a layer of adhesive introduced between them, the adhesive matrix of the adhesive layer containing nanoscale particles.

The present invention also relates to a process for dissolving adhesive bonds using electrical, magnetic or electromagnetic alternating fields, the adhesive layer containing nanoscale particles, which heat the adhesive layer under the influence of these alternating fields. The effect of this heating of the adhesive layer is to separate the adhesive bonds. In this connection, the nanoscale particles act as fillers with "signal receiver" properties so that energy in the form of electromagnetic alternating fields is purposefully introduced into the adhesive bond. The introduction of energy into the adhesive results in a local increase in temperature so that the adhesive bond can be reversibly dissolved. In the case of nonreactive thermoplastic adhesive systems, this introduction of energy results in melting of the adhesive polymer; in the case of reactive, i.e. crosslinked, thermoset adhesive systems, the increase in temperature leads to thermal degradation of the polymer and hence to a break in the adhesive joint. In this connection, particularly preferred adhesives are those which are either thermally labile themselves or of which the polymer backbone contains individual thermally labile groups. The modification of adhesives with thermally labile additives, which can be activated by an increase in temperature and which thus initiate failure of the adhesive, may also be successfully used for the dissolvable adhesive bonds according to the invention.

The process according to the invention is useful because heat is generated locally in the adhesive joint and that exposure of the bonded substrate materials (beauty-product and/or nail, lash, or scalp) themselves to heat is avoided or minimized. This is effective because the heat does not have to be introduced into the adhesive joint through the bonded substrates by diffusion processes.

Electrical alternating fields or magnetic alternating fields are suitable for the introduction of energy. Where electrical alternating fields are applied, suitable filler materials are any piezoelectric compounds, for example quartz, tourmaline, barium titanate, lithium sulfate, potassium (sodium) tartrate, ethylenediamine tartrate, ferroelectric materials of perovskite structure and, above all, lead zirconium titanate. Where magnetic alternating fields are used, any ferrimagnetic, ferromagnetic or superparamagnetic materials are basically suitable, more particularly the metals aluminium, cobalt, iron, nickel or alloys thereof and metal oxides of the n-maghemite type ($\gamma$-$Fe_2O_3$) and the n-magnetite type ($Fe_3O_4$), ferrites with the general formula $MeFe_2O_4$, where Me stands for divalent metals from the group consisting of copper, zinc, cobalt, nickel, magnesium, calcium or cadmium.

Where magnetic alternating fields are used, nanoscale superparamagnetic particles, so-called single domain particles, are particularly suitable. Compared with the paramagnetic particles known from the prior art, the nanoscale fillers are distinguished by the fact that they have no hysteresis. The result of this is that the dissipation of energy is not produced by magnetic hysteresis losses, instead the generation of heat is attributable to an oscillation or rotation of the particles in the surrounding matrix induced during the action of an electromagnetic alternating field and, hence, ultimately to mechanical friction losses. This leads to a particularly effective heating rate of the particles and the matrix surrounding them.

A corresponding process for the production of agglomerate-free nanoscale particles, for example iron oxide particles, is described in columns 8 to 10 of DE-A-196 14 136. Methods for the surface coating of such nanoscale particles for avoiding agglomeration thereof are disclosed in DE-A-197 26 282.

In principle, any polymers suitable for adhesives may be used as the binder matrix for the adhesives according to the invention. Examples of thermoplastically softenable adhesives are hotmelt adhesives based on ethylene/vinyl acetate copolymers, polybutenes, styrene/isoprene/styrene and styrene/butadiene/styrene copolymers, thermoplastic elastomers, amorphous polyolefins, linear thermoplastic polyurethanes, copolyesters, polyamide resins, polyamide/EVA copolymers, polyaminoamides based on dimer fatty acids, polyester amides or polyether amides. Other suitable adhesive matrixes are, in principle, the known two-pack adhesives based on one- or two-component polyurethanes, one- or two-component polyepoxides, silicone polymers (one or two components), the silane-modified polymers described, for example, in G. Habenicht "KLeben: Grundlagen, Technologie, Anwendungen", 3rd Edition, 1997, Chapter 2.3.4.4. The (meth)acrylate-functional two-pack adhesives based on peroxidic hardeners, anaerobic curing mechanisms, aerobic curing mechanisms or UV curing mechanisms are also suitable as the adhesive matrix. Actual examples of the incorporation of thermally labile groups in two-pack adhesives for the purpose of subsequently splitting these bonds are the adhesives according to WO 99/07774 of which at least one component contains disulfide or polysulfide bonds. In one particularly preferred embodiment, these adhesives may also contain solid splitting reagents in crystalline, encapsulated, chemically blocked, topologically or sterically inactivated or kinetically inhibited, finely dispersed form, as disclosed on pages 14 to 16 of hitherto unpublished DE-A-199 04 835.6.

In principle, any relatively high-frequency electromagnetic alternating field may be used as the energy source for heating the nanoscale particles see, for example, Kirk-Othmer, "Encyclopedia of Chemical Technology", 3rd Edition, Vol. 15, chapter entitled "Microwave technology".

It was pointed out in the foregoing that, where nanoscale particles according to the invention are used, electromagnetic radiation may be used to particular effect. This is clearly reflected in the fact that, even in the low-frequency range of about 50 kHz or 100 kHz up to 100 MHz, virtually any frequency can be used to produce the amount of heat needed to split the adhesive bond matrix in the adhesive matrix. The choice of the frequency may be determined by the equipment available, care naturally having to be taken to ensure that interference fields are not radiated.

Those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

The invention claimed is:

1. A beauty care product system, comprising:
   (a) an energy releasable beauty care product selected from an artificial nail, nail gel or nail polish; and
   (b) an adhesive layer comprising energy-expandable microspheres such that (a) is removable through the utilization of an energy source;
   wherein the adhesive layer attaches the energy-releasable beauty care product of (a) to an attached fingernail and wherein, upon application of an energy source to the energy-releasable beauty care product, the energy-expandable microspheres swell, breaking the attachment between the adhesive layer and the fingernail.

2. The beauty care product system of claim 1, further comprising an energy converter, wherein said energy converter comprises a member of the group consisting of (i) electrically conductive particles; and (ii) a foil or film made of a conductive or magnetic material.

3. The beauty care system of claim 2, wherein, upon the application of an energy source, the energy converter generates thermal energy sufficient to cause the energy-expandable microspheres to increase in size, breaking the adhesive attachment between the beauty care product and the fingernail to which the adhesive layer was attached.

4. The beauty care system of claim 2, further comprising an energy source, wherein, upon the activation of the energy source, the energy converter generates thermal energy sufficient to cause the energy-expandable microspheres to increase in size, breaking the adhesive bonds between the beauty care product and the fingernail to which the adhesive layer was attached.

5. The beauty care system of claim 4, wherein the energy source is an electrical, magnetic, electromagnetic, light, or heat source.

6. The beauty care system of claim 1, wherein the energy-expandable microspheres are incorporated into thermally expanding particles or liquid drops.

7. The beauty care system of claim 6, wherein the thermally expanding particles or liquid drops are incorporated into an adhesive material.

8. The beauty care system of claim 4, wherein the energy converter comprises a foil or a film.

9. The beauty care system of claim 8, wherein the foil or film generates heat when subjected to an external energy source.

10. The beauty care system of claim 9, wherein the external energy source provides electrical and/or magnetic energy.

11. The beauty care system of claim 6, wherein thermally expanding particles or liquid drops have an average diameter of 1 to 100 micrometers.

12. The beauty care system of claim 6, wherein thermally expanding particles or liquid drops have an average diameter of 5 to 40 micrometers.

13. The beauty care system of claim 7, wherein thermally expanding particles or liquid drops have an average diameter of 1 to 100 micrometers.

14. The beauty care system of claim 7, wherein thermally expanding particles or liquid drops have an average diameter of 5 to 40 micrometers.

* * * * *